United States Patent
Nita et al.

(12)

(10) Patent No.: US 6,702,748 B1
(45) Date of Patent: Mar. 9, 2004

(54) CONNECTOR FOR SECURING ULTRASOUND CATHETER TO TRANSDUCER

(75) Inventors: Henry Nita, Redwood Shores, CA (US); Martinos Tran, Tracy, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 0 days.

(21) Appl. No.: 10/251,227

(22) Filed: Sep. 20, 2002

(51) Int. Cl.$^7$ ................................. A61B 8/14
(52) U.S. Cl. ..................................... 600/459
(58) Field of Search .................. 600/407–471; 73/620–633; 606/167–171, 180; 604/22, 19–21, 96, 102, 113, 282, 283; 601/2, 3; 128/897, 916

(56) References Cited

U.S. PATENT DOCUMENTS 5,417,672 A    5/1995  Nita et al.
5,989,208 A  * 11/1999  Nita .......................... 604/22

\* cited by examiner

Primary Examiner—Ali M. Imam
(74) Attorney, Agent, or Firm—Raymond Sun

(57) ABSTRACT

A connector assembly connects an ultrasound transducer to an ultrasound catheter that has an ultrasound transmission member extending longitudinally therethrough. The connector assembly has an ultrasound transducer having a transducer housing, and an extension having a proximal end attached to the distal end of the transducer housing. The connector assembly also includes a ring assembly having an inner ring and an outer ring that is received inside the bore of the outer ring. The connector assembly also includes a catheter knob having a proximal end that is removably coupled to the extension. The inner ring is moved from a non-supporting position with the extension positioned inside the bore of the inner ring, to a supporting position with the catheter knob positioned inside the bore of the inner ring.

14 Claims, 6 Drawing Sheets

CONNECTOR FOR SECURING ULTRASOUND CATHETER TO TRANSDUCER

BACKGROUND OF THE INVENTION

1. Field of the Invention

The present invention pertains to medical equipment, and more particularly, to a device and method for attaching an ultrasound catheter to an ultrasound transducer which mitigates against breakage of the ultrasound transmission member, and which facilitates ultrasound energy propagation.

2. Description of the Prior Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, requires the use of relatively small diameter ultrasound catheters which are sufficiently small and flexible to undergo transluminal advancement through the tortuous vasculature of the aortic arch and coronary tree. However, because of its small diameter, the ultrasound transmission member which extends through such catheters is particularly susceptible to breakage and losses in the transmitted ultrasound energy.

Breakage of ultrasound transmission members often occurs near the proximal end thereof, generally at the coupling between the ultrasound catheter coupling and the ultrasound transducer. This is believed to be because energy concentrations are highest at these points. Thus, any external forces applied to the ultrasound transmission member in this region may result in stresses exceeding the elastic limit of the ultrasound transmission member.

External forces may be inadvertently and undesirably applied to the ultrasound transmission member by pressing upon, pushing, pulling, torquing, bending or bumping the ultrasound transmission member coupling during use of the ultrasound catheter. Such forces when applied to the ultrasound catheter coupling area result in limited ultrasound energy transmission through the ultrasound transmission member. If ultrasound energy is being transmitted by the ultrasound transmission member at the instant such forces are applied thereto, stresses occur which commonly result in breakage of the ultrasound transmission member.

Thus, there still exists a need to mitigate against breakage of the ultrasound transmission member by reducing mechanical stress applied to the proximal end of the ultrasound transmission member during operation.

SUMMARY OF THE DISCLOSURE

It is an object of the present invention to provide an ultrasound catheter system that mitigates against breakage of the ultrasound transmission member by reducing mechanical stress applied to the proximal end of the ultrasound transmission member during operation.

It is another object of the present invention to provide an improved connection between the ultrasound catheter and the ultrasound transducer.

It is yet another object of the present invention to improve the propagation of ultrasound energy by limiting and minimizing impact of undesirable external forces.

In order to accomplish the objects of the present invention, there is provided a connector assembly for connecting an ultrasound transducer to an ultrasound catheter that has an ultrasound transmission member extending longitudinally therethrough. The connector assembly has an ultrasound transducer having a transducer housing, and an extension having a proximal end attached to the distal end of the transducer housing. The connector assembly also includes a ring assembly having an inner ring and an outer ring that is received inside the bore of the outer ring. The connector assembly also includes a catheter knob having a proximal end that is removably coupled to the extension. The inner ring is moved from a non-supporting position with the extension positioned inside the bore of the inner ring, to a supporting position with the catheter knob positioned inside the bore of the inner ring.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
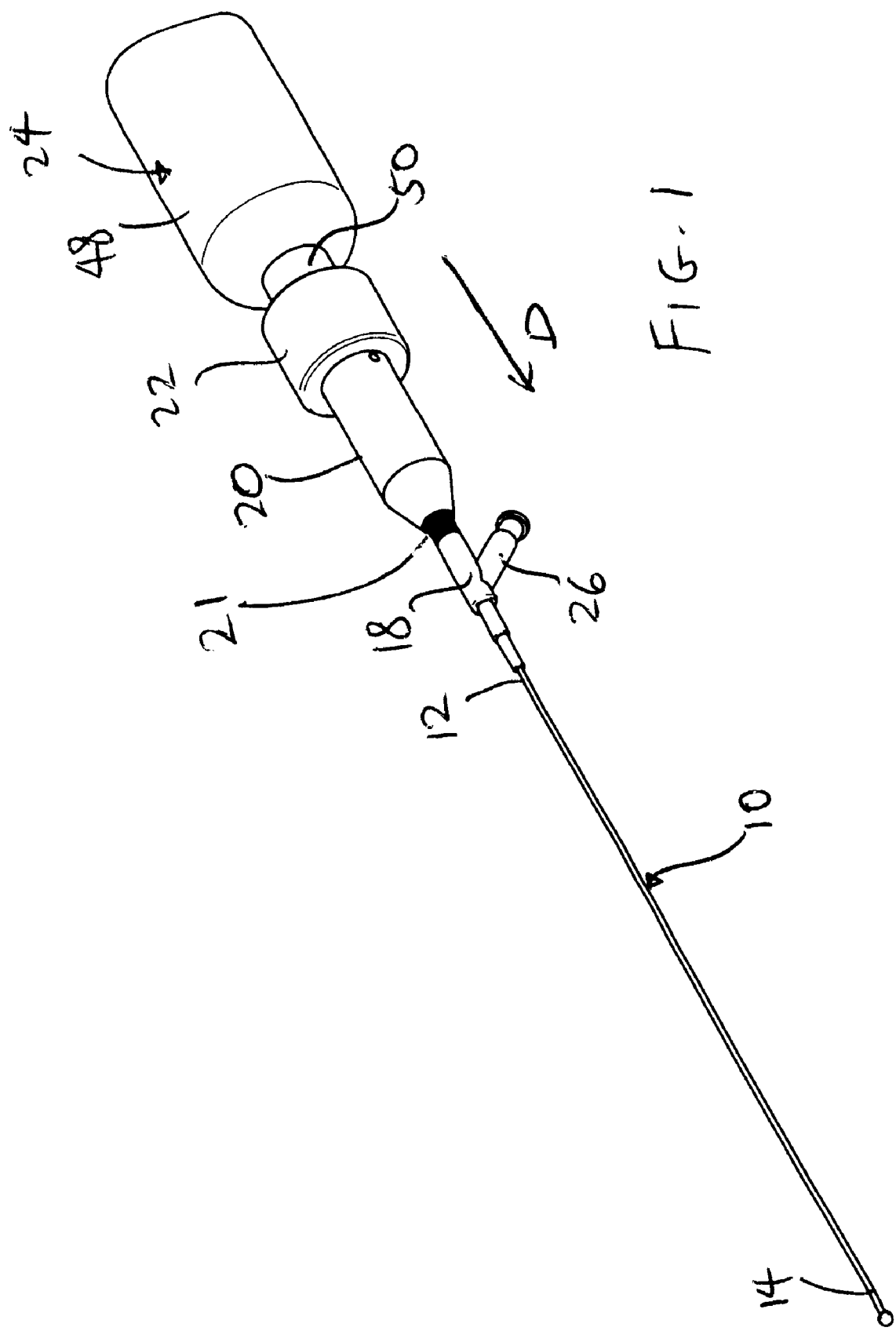
FIG. 1 is a perspective view of an ultrasound catheter attached to an ultrasound transducer according to one embodiment of the present invention, shown with the ring assembly in the supporting position.
Figure 6:
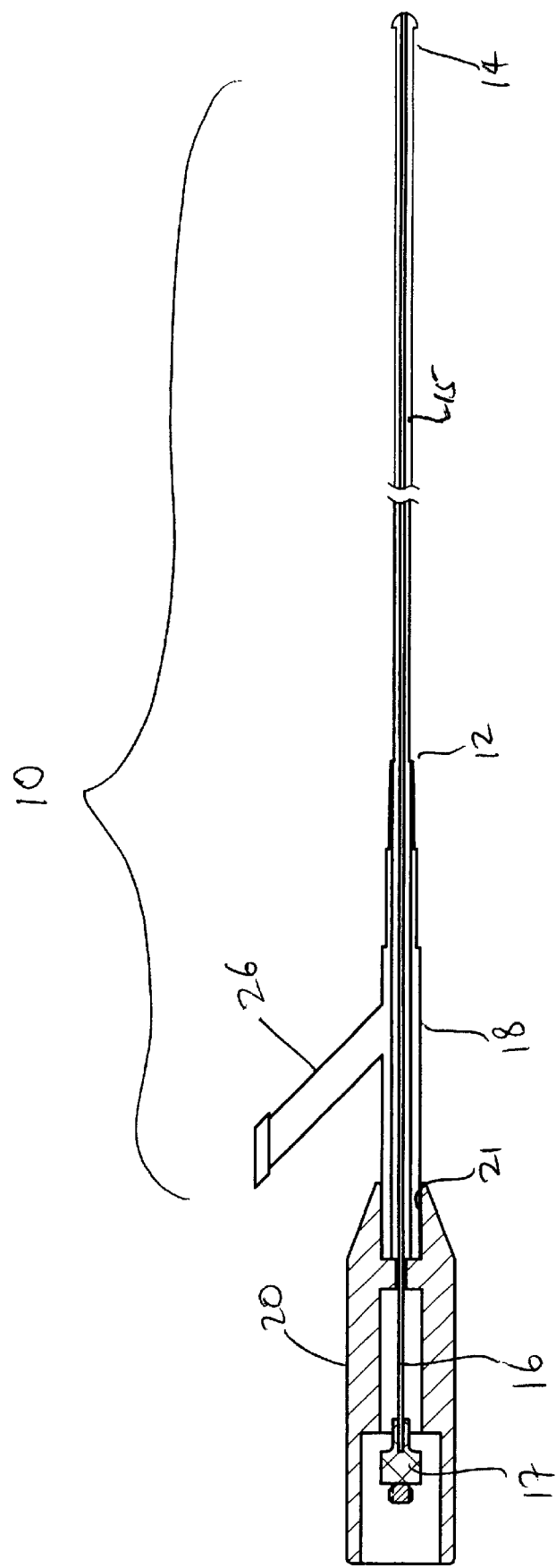
FIG. 6 is a cross-sectional side view of the ultrasound catheter of FIG. 1.

FIG. 1 illustrates an ultrasound catheter 10 that can be used for ablating and removing occlusive material inside the vessel of an animal or human being. The ultrasound catheter 10 has a proximal end 12 and a distal end 14, and defines at least one lumen 15 (see FIG. 6) extending longitudinally therethrough. An ultrasound transmission member 16 (see FIGS. 4A, 4B and 6) extends through the lumen 15 of the catheter 10 from the distal end 14 to the proximal end 12. The ultrasound catheter 10 is operatively coupled at its proximal end 12, by way of a Y-connector 18, a catheter knob 20, and a ring assembly 22, to an ultrasound transducer housing 24. An ultrasound transducer 25 is positioned inside the transducer housing 24, and is connected to a signal generator (not shown), which operates to send an electrical signal to the ultrasound transducer 25, which converts the electrical signal to ultrasound energy. The ultrasound transducer 25 is coupled via a sonic connector 17 (described in greater detail below) to the ultrasound transmission member 16, so that the ultrasound energy can be passed through the sonic connector 17 and the ultrasound transmission member 16 to be delivered to the distal end 14 of the catheter 10. A guidewire (not shown), which can be any conventional monorail or over-the-wire guidewire, may be utilized in conjunction with the catheter 10 in a manner that is well-known in the catheter art.

The frontal portion of the Y-connector 18 is connected to the proximal end 12 of the catheter 10 using techniques that are well-known in the catheter art. An injection pump (not shown) or IV bag (not shown) can be connected, by way of an infusion tube (not shown), to an infusion port or sidearm 26 of the Y-connector 18. The injection pump can be used to infuse coolant fluid (e.g., 0.9% NaCl solution) into and/or through the lumen 15 of the catheter 10. Such flow of coolant fluid may be utilized to prevent overheating of the ultrasound transmission member 16 extending longitudinally through the lumen 15. Such flow of the coolant fluid through the lumen 15 of the catheter 10 serves to bathe the outer surface of the ultrasound transmission member 16, thereby providing for an equilibration of temperature between the coolant fluid and the ultrasound transmission member 16. Thus, the temperature and/or flow rate of coolant fluid may be adjusted to provide adequate cooling and/or other temperature control of the ultrasound transmission member 16. In addition to the foregoing, the injection pump may be utilized to infuse a radiographic contrast medium into the catheter 10 for purposes of imaging. Examples of iodinated radiographic contrast media which may be selectively infused into the catheter 10 via the injection pump are commercially available as Angiovist 370 from Berlex Labs, Wayne, N.J. and Hexabrix from Malinkrodt, St. Louis, Mo.

The proximal end of the ultrasound transmission member 16 is attached to a sonic connector 17 which is configured to effect operative and removable attachment of the proximal end of the ultrasound transmission member 16 to the horn 19 of the ultrasound transducer 25. The sonic connector 17 is preferably configured and constructed to permit passage of ultrasound energy through the ultrasound transmission member 16 with minimal lateral side-to-side movement of the ultrasound transmission member 16 while, at the same time, permitting unrestricted longitudinal forward/backward vibration or movement of the ultrasound transmission member 16.

The ultrasound transmission member 16 may be formed of any material capable of effectively transmitting the ultrasonic energy from the ultrasound transducer 25 to the distal end 14 of the catheter 10, including but not necessarily limited to metal, plastic, hard rubber, ceramic, fiber optics, crystal, polymers, and/or composites thereof. In accordance with one aspect of the invention, all or a portion of the ultrasound transmission member 16 may be formed of one or more materials which exhibit super-elasticity. Such materials should preferably exhibit super-elasticity consistently within the range of temperatures normally encountered by the ultrasound transmission member 16 during operation of the catheter 10. Specifically, all or part of the ultrasound transmission member 16 may be formed of one or more metal alloys known as "shape memory alloys". Such superelastic metal alloys are well-known in the art and will not be described in any further detail herein.

The proximal end of the Y-connector 18 is attached to the distal end of the catheter knob 20 by threadably engaging the proximal end of the Y-connector 18 inside a threaded distal bore 21 at the distal end of the catheter knob 20. The proximal end of the catheter knob 20 is received by the ring assembly 22 and the distal end of the transducer housing 24. The ring assembly 22 is positioned over the distal end of the transducer housing 24, and has a non-supporting position where the ring assembly 22 is retracted towards the transducer housing 24, and has a supporting position where the ring assembly 22 is extended to engage at least a portion of the catheter knob 20. The ring assembly 22 functions as a support member that is disposed on the transducer housing 24 to support at least a portion of the catheter knob 20.

Figure 2:
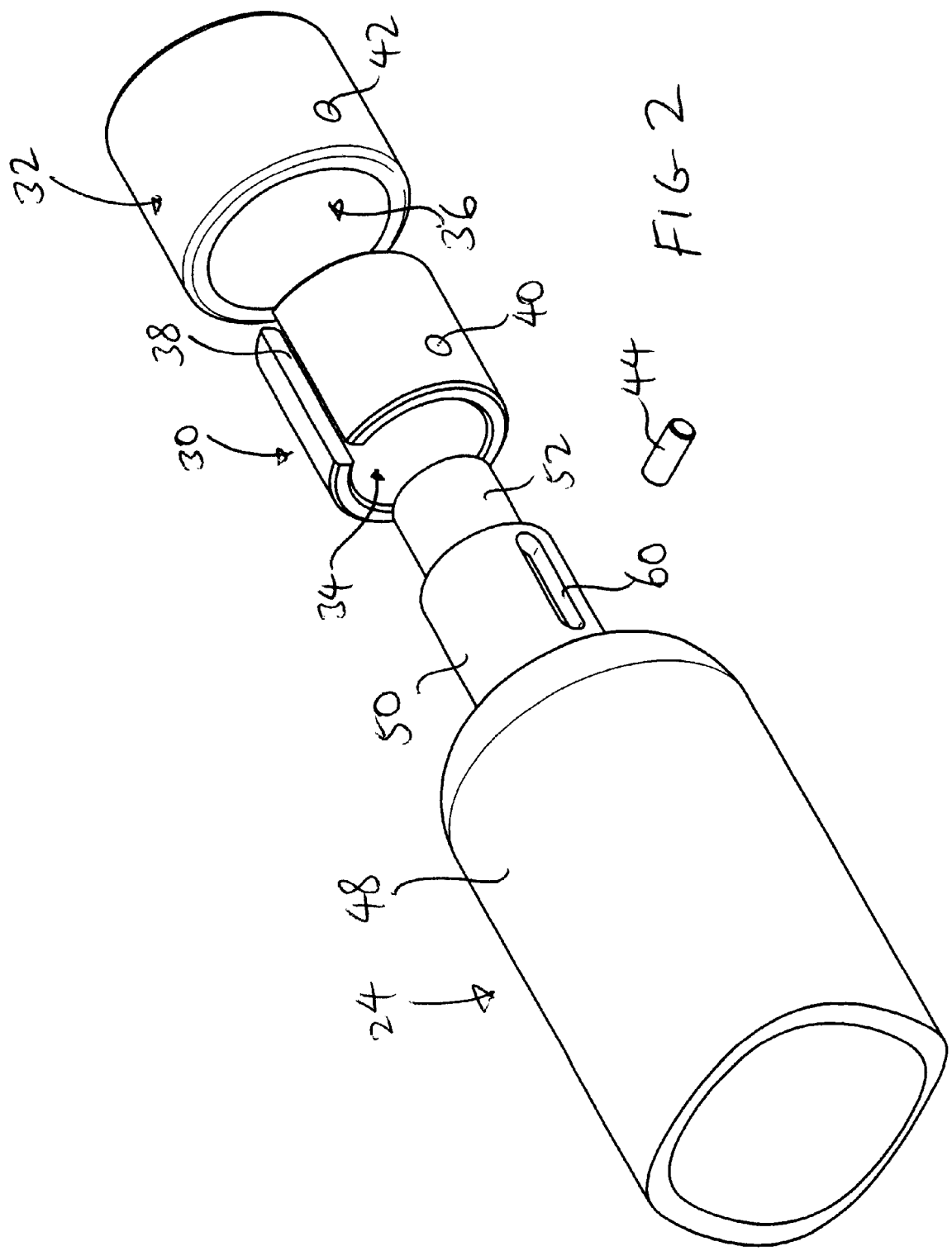
FIG. 2 is an exploded perspective view illustrating the various elements of the ring assembly and the transducer housing of the system of FIG. 1.
Figure 3:
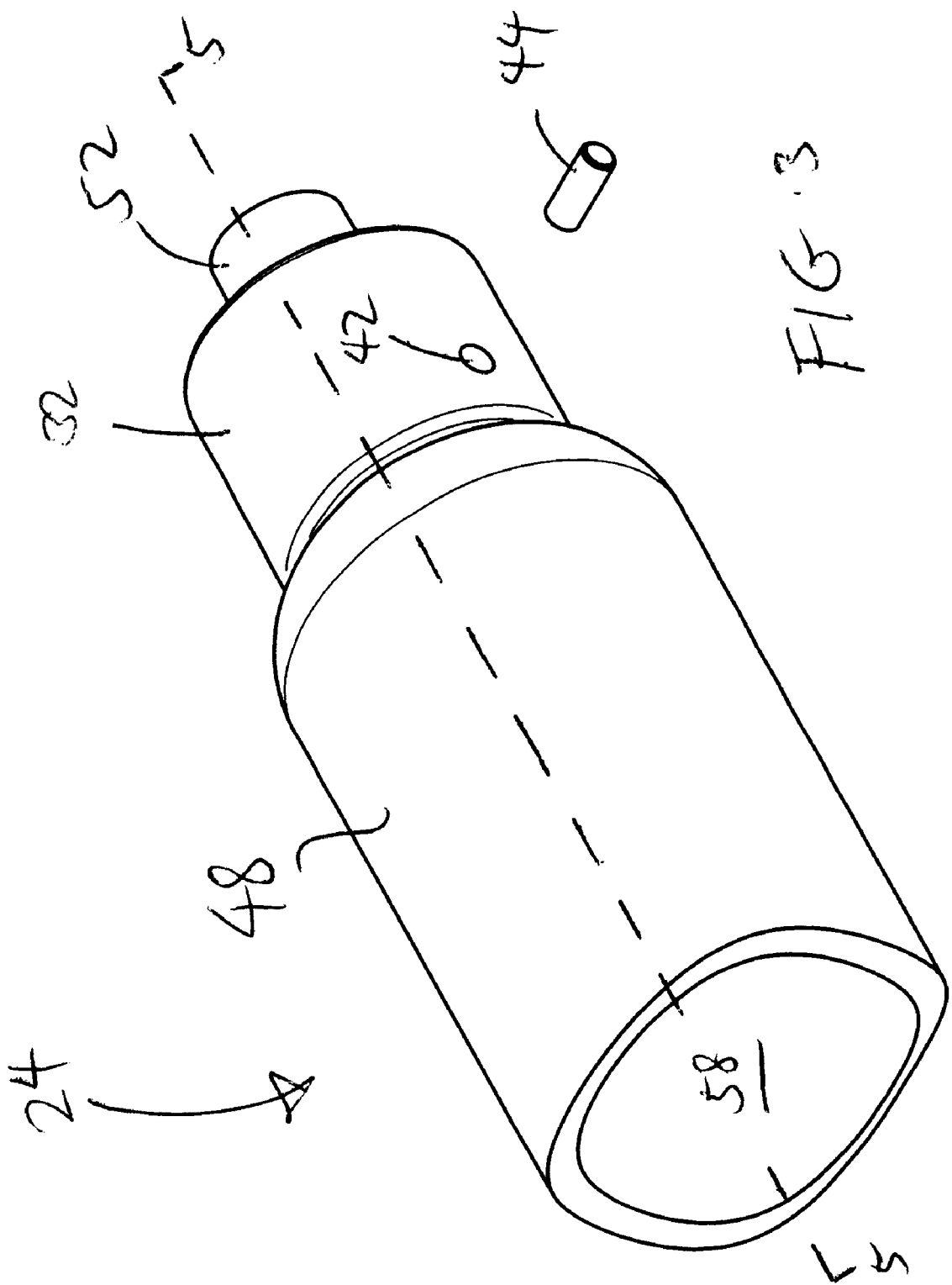
FIG. 3 is a perspective view of the ring assembly and the transducer housing of FIG. 2 shown with the ring assembly in the non-supporting position.

Referring to FIG. 2, the ring assembly 22 has an inner ring 30 and an outer ring 32. The inner ring 30 has a bore 34 and a longitidunal slit 38 that extends through the length of the inner ring 30. The distal portion of the bore 34 can be tapered for receiving the catheter knob 20 in a manner which more tightly grips the catheter knob 20 as the inner ring 30 is moved from the non-supporting position to the supporting position. The outer ring 32 also has a bore 36. Each of the inner ring 30 and the outer ring 32 has an opening 40 and 42, respectively, that are aligned with each other and that are adapted to receive a locking pin 44.

Figure 4:
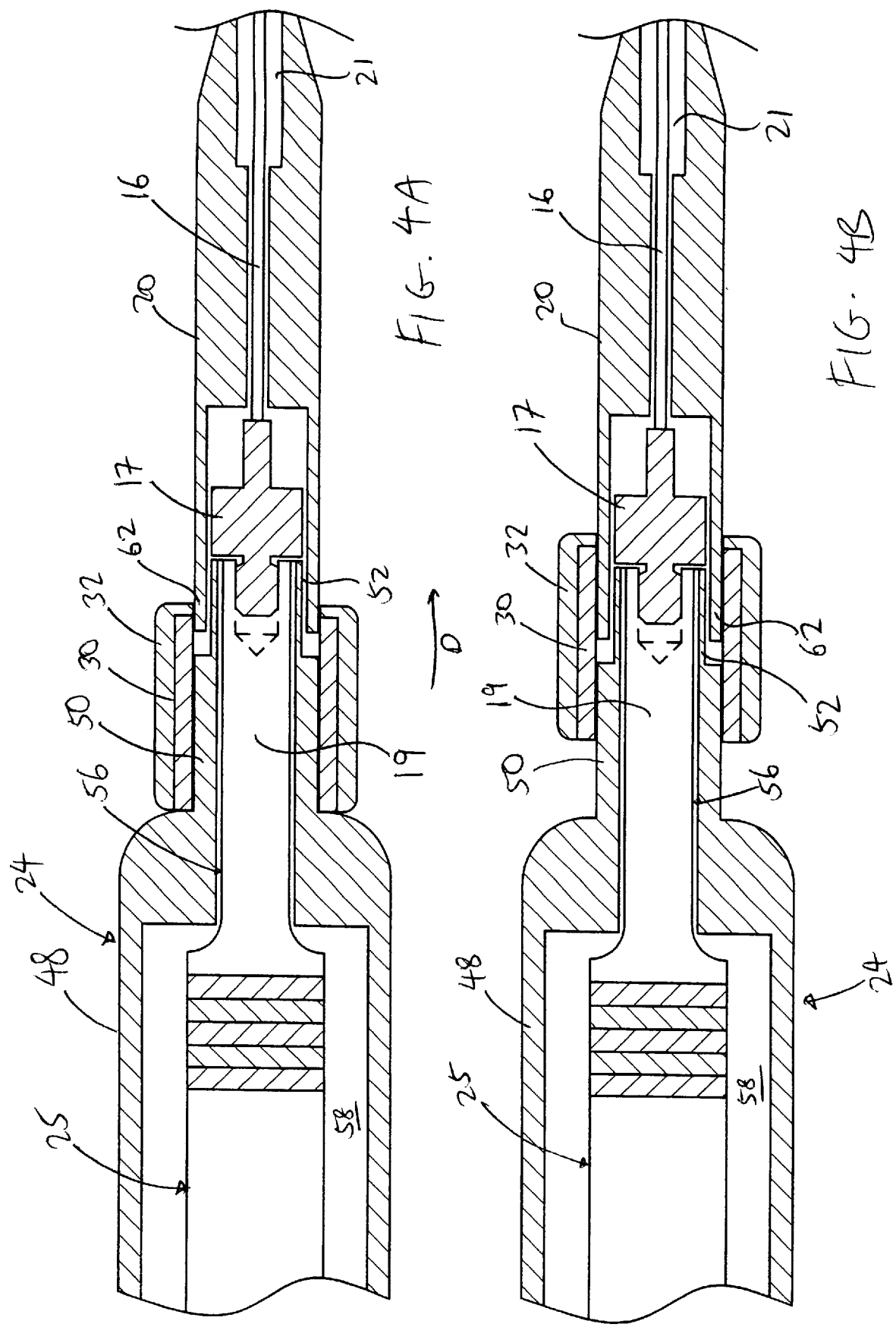
FIG. 4A is a cross-sectional side view taken along lines 5—5 in FIG. 3 illustrating the ring assembly in the supporting position, and also illustrating the transducer and catheter knob.
FIG. 4B is a cross-sectional side view taken along lines 5—5 in FIG. 3 illustrating the ring assembly in the non-supporting position, and also illustrating the transducer and catheter knob.

Referring now to FIGS. 2, 3, 4A and 4B, the transducer housing 24 has a cylindrical wall 48 having two stepped cylindrical extensions 50 and 52 extending from the distal end of the housing 48. The first extension 50 is attached to the distal end of the cylindrical wall 48, and has a greater outer diameter than the second extension 52 that is attached to the distal end of the first extension 50. A throughbore 56 extends from the hollow interior 58 of the cylindrical wall 48 and through the extensions 50 and 52. The throughbore 56 can have the same diameter throughout its length. The first extension 50 is adapted to be received inside the bore 34 of the inner ring 30, while the second extension 52 is adapted to couple the proximal end of the catheter knob 20. In particular, the catheter knob 20 can be generally cylindrical having a hollow interior so that the proximal end 62 of the catheter knob 20 can be sleeved over the second extension 52 in a manner such that the outer surface of the catheter knob 20 can be substantially flush with the outer surface of the first extension 50, as best shown in FIGS. 4A and 4B.

A longitudinal close ended slot 60 is provided on the first extension 50 for receiving the pin 44. The pin 44 extends through the openings 40, 42 and is then inserted in the slot 60, with the slot 60 defining the two limits of movement for the ring assembly 22, thereby defining the non-supporting position and the supporting position.

Thus, the ring assembly 22 functions as a support member that is disposed on the transducer housing 24 to support at least a portion of the catheter knob 20. Supporting of at least a portion of the catheter knob 20 mitigates against breakage of the ultrasound transmission member 16 by reducing mechanical stress applied to the proximal end thereof, particularly when ultrasound energy propogates through the ultrasound transmission member 16. The ring assembly 22 tends to mitigate or prevent the transmission of external forces (e.g., caused by pushing, bending, pulling, torquing or bumping the catheter knob 20) from the catheter knob 20 to the proximal end of the ultrasound transmission member 16 extending therethrough.

Figure 5:
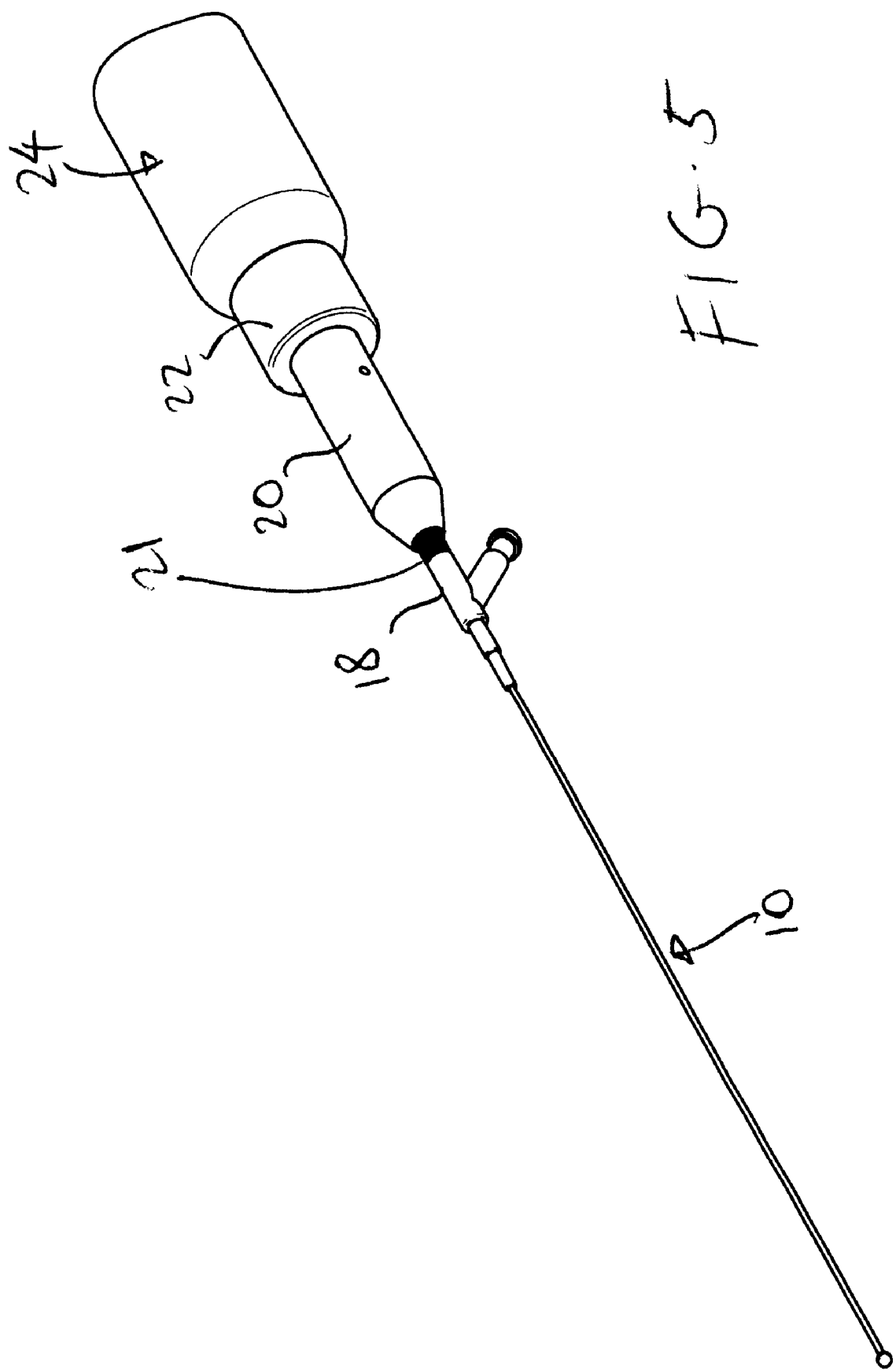
FIG. 5 is a perspective view of the ultrasound catheter and the transducer housing shown with the ring assembly in the non-supporting position.

To use the ring assembly 22 of the present invention, the outer ring 32 is normally positioned over the inner ring 30 with the inner ring 30 seated in the bore 36 of the outer ring 32. The combined inner and outer rings 30, 32 are then positioned over the first extension 50 so that the inner and outer rings 30, 32 are positioned against the transducer housing 24 in the non-supporting position (see FIGS. 4A and 5). The proximal end 62 of the catheter knob 20 is then sleeved over the second extension 52 so that the second extension 52 is received inside the hollow interior of the catheter knob 20. In this regard, the inner surface of the proximal end 62 of the catheter knob 20 can have threads that removably engage corresponding threads provided on the outer surface of the second extension 52. At this time, the ring assembly 22 is moved in a distal direction (see arrow D in FIGS. 1 and 4A) so that the combined inner and outer rings 30, 32 are then positioned over the second extension 52 in the supporting position (see FIGS. 1 and 4B). As the ring assembly 22 is moved in a distal direction (see arrow D), the pin 44 slides along the slot 60, but the two opposing ends of the slot 60 define the two opposing limits of movement for the ring assembly 22. The transducer 25 is coupled to the sonic connector 17 using techniques that are well known in the art.

The combined inner and outer rings 30, 32 tightly grip and firmly engage the captured (proximal) portion 62 of the catheter knob 20 so as to provide substantial support thereto, thereby mitigating the impact of unwanted forces on the ultrasound transmission member 16. Upon completion of the therapeutic procedure, the ultrasound catheter 10 is removed from the transducer housing 24 by reversing the. above-described procedure. In particular, the combined inner and outer rings 30, 32 are retracted in a direction opposite to the direction of the arrow D so that the combined inner and outer rings 30, 32 are now positioned over the first extension 50 against the transducer housing 24 in the non-supporting position (see FIG. 6). The catheter knob 20 can then be separated from the second extension 52 by unthreading and pulling the proximal end of the catheter knob 20 from the second extension 52.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A connector assembly for connecting an ultrasound transducer to an ultrasound catheter, the connector assembly comprising:
   an ultrasound transducer having a transducer housing having a distal end, and an extension provided at the distal end of the transducer housing;
   a ring assembly having an inner ring that has a bore, and an outer ring that has a bore, with the inner ring received inside the bore of the outer ring;
   a catheter knob having a proximal end that is coupled to the extension; and
   wherein the inner ring is moved from a non-supporting position with the extension positioned inside the bore of the inner ring, to a supporting position with a portion of the catheter knob positioned inside the bore of the inner ring.

2. The assembly of claim 1, wherein the proximal end of the catheter knob is partially positioned inside the bore of the inner ring when the inner ring is in the supporting position.

3. The assembly of claim 1, wherein the extension has a smaller outer diameter than the transducer housing.

4. The assembly of claim 2, wherein the inner ring is positioned inside the bore of the outer ring when the inner ring is in the supporting position.

5. The assembly of claim 2, wherein the inner ring is positioned inside the bore of the outer ring when the inner ring is in the non-supporting position.

6. The assembly of claim 1, wherein the extension has a longitudinal slot, and wherein each of the inner ring and the outer ring has an opening, with a pin extending through the opening in the inner ring and the opening in the outer ring, and traveling within the slot.

7. The assembly of claim 1, wherein the extension comprises a first extension having a distal end and a proximal end attached to the distal end of the transducer housing, and a second extension having a distal end and a proximal end attached to the distal end of the first extension.

8. The assembly of claim 7, wherein the first extension has a greater outer diameter than the second extension.

9. An ultrasound system, comprising:
   a catheter having a hollow lumen therethrough, the catheter having a proximal end and a distal end;
   an ultrasound transducer having a transducer housing having a distal end, with a first extension having a distal end and a proximal end attached to the distal end of the transducer housing, a second extension having a distal end and a proximal end attached to the distal end of the first extension;
   a ring assembly having an inner ring that has a bore, and an outer ring that has a bore, with the inner ring received inside the bore of the outer ring;
   a catheter knob having a distal end that is attached to the proximal end of the catheter, and a proximal end that is removably coupled to the second extension;
   an ultrasound transmission member having a proximal end that is coupled to the transducer, the ultrasound transmission member extending through the catheter knob and the lumen of the catheter to the distal end of the catheter; and
   wherein the inner ring is moved from a non-supporting position with the first extension positioned inside the bore of the inner ring, to a supporting position with the second extension positioned inside the bore of the inner ring.

10. The system of claim 9, wherein the proximal end of the catheter knob is positioned inside the bore of the inner ring when the inner ring is in the supporting position.

11. The system of claim 9, wherein the first extension has a greater outer diameter than the second extension.

12. The system of claim 10, wherein the inner ring is positioned inside the bore of the outer ring when the inner ring is in the supporting position.

13. The system of claim 10, wherein the inner ring is positioned inside the bore of the outer ring when the inner ring is in the non-supporting position.

14. The system of claim 9, wherein the first extension has a longitudinal slot, and wherein each of the inner ring and the outer ring has an opening, with a pin extending through the opening in the inner ring and the opening in the outer ring, and traveling within the slot.

* * * * *